(12) United States Patent
Senosiain Peláez et al.

(10) Patent No.: US 9,186,342 B2
(45) Date of Patent: Nov. 17, 2015

(54) COMBINATION OF AN NSAID AND AN AMINO ACID

(75) Inventors: Juan Pablo Senosiain Peláez, Colonia Anahuac (MX); Angélica Arzola Paniagua, Colonia Anahuac (MX); Enrique Raúl García-Salgado López, Colonia Anahuac (MX)

(73) Assignee: LABORATORIOS SENOSIAIN S.A. DE C.V., Distrito Federal (MX)

( * ) Notice: Subject to any disclaimer, the term of this patent is extended or adjusted under 35 U.S.C. 154(b) by 254 days.

(21) Appl. No.: 13/696,022

(22) PCT Filed: Apr. 28, 2011

(86) PCT No.: PCT/IB2011/000916
§ 371 (c)(1),
(2), (4) Date: Dec. 19, 2012

(87) PCT Pub. No.: WO2011/138653
PCT Pub. Date: Nov. 10, 2011

(65) Prior Publication Data
US 2013/0109754 A1    May 2, 2013

(30) Foreign Application Priority Data

May 4, 2010   (MX) .................... MX/a/2010/004974

(51) Int. Cl.
*A61K 31/198*     (2006.01)
*A61K 31/192*     (2006.01)

(52) U.S. Cl.
CPC ............. *A61K 31/198* (2013.01); *A61K 31/192* (2013.01)

(58) Field of Classification Search
CPC . A61K 31/192; A61K 31/198; A61K 47/183; A61K 31/19; A61K 47/02
USPC ........................................................ 514/565
See application file for complete search history.

(56) References Cited

U.S. PATENT DOCUMENTS 4,689,218 A    8/1987   Gazzaniga et al.
(Continued)

FOREIGN PATENT DOCUMENTS

CN          101889997 A     11/2010
WO      WO 03/039532 A1      5/2003

OTHER PUBLICATIONS

Black et al.; European Journal of Clinical Pharmacology; Sep. 2002, vol. 58, Issue 6, pp. 387-394; "Ibuprofen arginate provides effective relief from postoperative dental pain with a more rapid onset of action than ibuprofen".

(Continued)

*Primary Examiner* — Savitha Rao
(74) *Attorney, Agent, or Firm* — Birch, Stewart, Kolasch & Birch, LLP

(57) ABSTRACT

The invention relates to an oral pharmaceutical composition comprising the combination of an ibuprofen salt or S(+)-ibuprofen with L-arginine and/or the pharmaceutically acceptable salts thereof, and additionally pharmaceutically acceptable vehicles and/or excipients. The invention also relates to the method of producing the composition and to the use of said composition having synergic therapeutic activity, for treating moderate to severe inflammatory pain, fever and inflammation.

10 Claims, 4 Drawing Sheets

(56) References Cited

U.S. PATENT DOCUMENTS

| | | | |
|---|---|---|---|
| 4,834,966 A | * | 5/1989 | Gazzaniga et al. ............. 424/43 |
| 5,500,226 A | * | 3/1996 | Stroppolo et al. ............ 424/466 |
| 2003/0100612 A1 | | 5/2003 | Pavliv |

OTHER PUBLICATIONS

De Palma et al., "Ibuprofen-Arginine Generates Nitric Oxide and Has Enhanced Anti-Inflammatory Effects", Pharmacological Research, vol. 60, 2009, pp. 221-228.

\* cited by examiner

COMBINATION OF AN NSAID AND AN AMINO ACID

FIELD OF THE INVENTION

The present invention relates to A pharmaceutical combination comprising ibuprofen (in its simple form or as a salt), either the dextrorotatory enantiomer, the laevorotatory one, or a mixture of both, with L-arginine and/or their pharmaceutically acceptable salts. Additionally, it also refers to a pharmaceutical composition comprising ibuprofen (as the racemic mixture or the dextrorotatory stereoisomer, (+)S-ibuprofen), with L-arginine and/or its pharmaceutically acceptable salts, vehicles and/or pharmaceutically acceptable excipients; the manufacturing process of the composition and the use of said composition with synergistic therapeutic activity, indicated for the treatment of pain from moderate to severe, fever and inflammation.

BACKGROUND OF THE INVENTION

The treatment of pain having an inflammatory origin requires the use of different strategies, for example, the use of non steroidal ant i-inflammatory agents (NSAID's). However, depending on the pain extent, the only use of an NSAID is not capable of controlling pain satisfactorily, and additionally, important adverse effects may appear with the chronic use of these agents, especially gastric damage, gastric ulcers (Gambero et al., 2005).

The balanced or multimodal analgesia is a therapeutic approach for pain control, which is based on the combination of two or more analgesics (Dalhet, 1990). In this sense, the combination of ibuprofen, a non-steroidal anti-inflammatory agent, with different adjuvants, has been previously described.

Ibuprofen (IBU) is a non-steroidal anti-inflammatory analgesic (NSAID), relatively insoluble in water, soluble in organic solvents, with a melting point between 75 and 77° C. It has been demonstrated that ibuprofen is a potent, effective analgesic, useful in the treatment of pain from moderate to severe. Aside from its analgesic effect, it is a moderate anti-inflammatory and antipyretic agent.

Ibuprofen acts on the cyclooxygenase II enzyme, which intervenes in the process of inflammation and pain, with a plasma half life between 1.9 and 2.2 hours. Around 99% of ibuprofen is linked to albumin. It is metabolized in the liver, it has a bioavailability of from 49 to 73% when administered orally. Food reduces the absorption rate, but not the absorbed amount.

Ibuprofen belongs to the group of the 2-arylpropionic acids, it has two enantiomeric forms, R(−) and S(+), being the racemic ibuprofen one of the most used NSAIDs. The anti-inflammatory activity resides almost exclusively in the S(+) enantiomer. In vivo, ibuprofen undergoes chiral inversion, in such way that the inactive R enantiomer is converted into the active S isomer.

The commonly recommended oral dose of ibuprofen in adults is from 900 mg to 2400 mg per day, without exceeding 3,200 mg per day.

Arginine (ARG) is one of the twenty amino acids that form part of proteins, it is classified as a semi-essential amino acid. Arginine participates in the nitric oxide synthesis mechanism, which causes the relaxation of the blood vessels (vasodilatation).

This amino acid is involved in a plurality of activities of the endocrine glands, it can stimulate the immunologic function by increasing the number of leucocytes, it has a vasodilatator effect, moreover, it is involved in the synthesis of creatine, polyamines and DNA. It can decrease cholesterol levels, and stimulate the release of the growth hormone (somatotropine). It is also involved in collagen production.

Similarly to L-carnitine (L-CAR), L-arginine (L-ARG) is believed to have potentiating functions in the conversion of fatty acids into energy (muscular fuel). It can decrease cholesterol levels by improving the capacity of the circulatory apparatus, as well as stimulate the growth hormone release, reduce the body fat levels and facilitate the athletes' recovery due to its effects in withdrawing ammonia (muscular residue resulting from anaerobic exercise) from the muscles and converting it into urea, which is excreted through urine.

The combination of ibuprofen has already been described previously with different active agents. Previous clinical studies have disclosed that ibuprofen plus oxycodone or paracetamol provide analgesia and comfort to the patients, reducing the amount of ibuprofen required for managing pain, and thus, the gastropathological complications associated to its use.

Other previous studies have disclosed that ibuprofen arginate promotes a fast onset of the analgesic action, compared to ibuprofen alone (Black et al., Eur J Clin Pharmacol. 2002), basically due to the increase in the NSAID dissolution and absorption. However, there are no studies demonstrating, aside from the pharmacokinetical process (absorption), the existence of pharmacodynamical processes that favor the potentiation of the analgesic effect of ibuprofen with L-arginine. The present invention demonstrates, by means of a pre-clinic study, the pharmacodynamic progression exhibited by this composition, and additionally, it demonstrates a synergistic effect in the therapeutic activity of the combination of ibuprofen and L-arginine.

In Mexico, patent No. MX 181134, discloses a pharmaceutical composition having between 9% and 17% weight-weight (w/w) ibuprofen, combined with between 17% and 33% w/w arginine, as well as between 20%-25% w/w sodium or potassium bicarbonate, and between 25%-40% w/w sodium bitartrate, wherein up to 40% arginine is substituted by lysine. This composition is in the form of an effervescent tablet o granulate that additionally contains sweeteners and flavoring agents.

In contrast with the formulation described in patent No. MX181134, the present invention evidences synergism between two components. Additionally, the preferred interval claimed in the present invention is outside the compositions claimed by patent No. MX181134.

Patent No. MX190245 discloses a pharmaceutical composition with analgesic activity, which is adequate for manufacturing pharmaceutical preparations with complete solubility in water, characterized because it comprises from 33% to 46% w/w ibuprofen; from 34% to 51% w/w L-arginine and from 9% to 29% w/w sodium bicarbonate, wherein the molar ratio between ibuprofen and L-arginine is between 1:1.1 and 1:1.5, and the weight ratio between ibuprofen and sodium bicarbonate is between 1:0.251 and 1:0.75; said composition is in the form of an effervescent granulate that additionally contains sweeteners and flavoring agents. Moreover, the combination of the present invention is not preferred as effervescent formulations.

In contrast with the formulation described in patent No. MX190245, the present invention evidences synergism between two components.

Patent MX241292 presents a pharmaceutical composition comprising an aqueous solution of arginine and ibuprofen, wherein the molar ratio arginine to ibuprofen is lower than 1:1 and the aqueous solution is sterilized and lyophilized; ibuprofen may be (RS)-Ibuprofen or (S)-Ibuprofen and arginine may be L-arginine or D-arginine. This composition can be administered by intravenous, intramuscular and oral route.

In contrast with this formulation, the present invention refers specifically to a non-sterile combination of ibuprofen and L-arginine, in a pharmaceutical form that is preferably solid, wherein the selected ratio allows obtaining a synergistic effect in its therapeutic activity, and wherein the preferred ibuprofen/L-arginine ratio is between 1.6 and 5.6. This feature allows decreasing the use of active agents, as well as their possible adverse effects, without reducing its therapeutic activity.

To date, there are commercial pharmaceutical formulations comprising ibuprofen arginate. These formulations can be found in the form of effervescent granules with 400 mg and 600 mg or as an ibuprofen arginate formulation in injectable solution in presentations of 400 mg and 800 mg. Ibuprofen and arginine are present in equimolar ratio in the ibuprofen arginate salt, said proportion is outside the synergistic interval of the present invention. Therefore, the mentioned formulations have an additive therapeutic effect, whereas the combination of the present invention presents a synergistic effect, which allows obtaining formulations with a lower amount of the active agents and with the same analgesic-anti-inflammatory and antipyretic therapeutic effect.

We have discovered that the effective dose at 30% (ED-30) of the ibuprofen-L-arginine association, $ED_{30}$ (experimental) is 52.05±0.07 mg/Kg, which is considerably lower than the theoretical $ED_{30}$ of 80.6±7.6 mg/Kg. The above result suggests that after oral co-administration of ibuprofen and L-arginine, the same level of analgesic effect is achieved (30% anti-nociceptive) but it can be reduced in about 1.5 times the dose of both drugs. For this reason, the present invention discloses the active agents preferably having an ibuprofen/L-arginine ratio of 1.6 to 5.6.

With this combination it is possible to preserve the therapeutic effect by reducing the amount of ibuprofen and its possible adverse effects, such as nausea, diarrhea, abdominal pain, dizziness, gastric hyperacidity, constipation, headache and some other less frequent effects, such as edema, fever, rash and blurred vision.

JUSTIFICATION OF THE INVENTION

Considering the aforementioned, it is convenient to have available a combination that attends the conditions of moderate to severe pain without provoking the adverse effects of NSAIDs. The combination of ibuprofen and L-arginine can be in the form of different pharmaceutical compositions, the preferred one being solid. The combination of ibuprofen and L-arginine of the present invention is directed to attend conditions of moderate to severe pain and neuralgias in different body sites, and it has a lower risk of provoking adverse effects, due to the use of a lower dose compared to the commonly used dose of ibuprofen.

In order to confirm the synergistic effect of the combination, the assessment and combination parameters of ibuprofen and L-arginine were established, by developing a pre-clinic study in rats and by constructing isobolograms among the combined therapeutic effects of ibuprofen and L-arginine.

BRIEF DESCRIPTION DE THE DRAWINGS

The attached figures illustrate the behavior of the drugs when being administered to the studied subjects.

FIG. 1 is a graph that compares the theoretical $ED_{30}$ effect versus the experimental $ED_{30}$ obtained with a formulation of the combination of ibuprofen and L-arginine. The experimental $ED_{30}$ (52.05±0.07 mg/kg) is considerably lower than the theoretical $ED_{30}$ (80.6±7.6 mg/kg), which indicates that the combination of ibuprofen and L-arginine produced synergism in the anti-nociceptive effect in the inflammatory pain model in rats ($p<0.05$).

FIG. 2 shows an isobologram of the systemic interaction between ibuprofen and L-arginine in the anti-nociceptive effect in the formalin test. The symbols show the experimental dose and the theoretical dose for the ratio IBU/L-ARG=3.26, where a significant synergism is demonstrated.

FIG. 3 exhibits the assessment of the comparative effect of the ibuprofen+L-arginine combination in different proportions, for the second phase of the inflammatory pain model produced by formalin.

Figure 7:
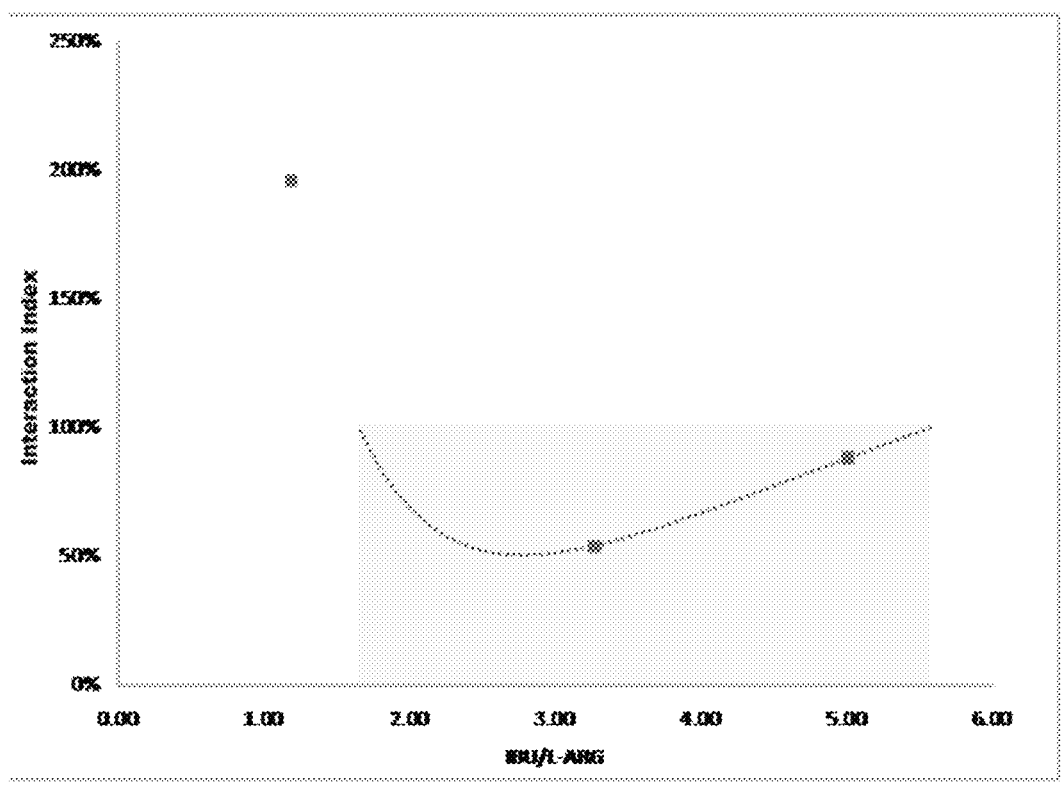

FIG. 7 is a graph showing the interaction index for the anti-nociceptive effect resulting from the administration of the combination of ibuprofen and L-arginine in different proportions. The dots represent sets of experimental data, whereas the line represents an interpolation as described in the text. The shaded zone represents the composition interval which is expected to have a synergistic behavior.

DESCRIPTION OF THE INVENTION

In accordance with the present invention, a combination comprising synergistically effective amounts of ibuprofen and L-arginine is provided. We have discovered that the concomittant administration of these two drugs in an ibuprofen/L-arginine ratio of 1.6 to 5.6, conducts to a synergistic effect in its anti-inflammatory, anti-nociceptive and anti-pyretic action.

The challenge during the development of the present invention, was to decrease the dose of the NSAID that is commonly used against pain, fever and inflammation, by combining it with another active agent which is secure and effective. In such a way, the combined dose of both ingredients is decreased by means of a synergistic effect, as well as possible adverse effects associated with the monodrugs.

A way of determining the effect of L-arginine on the anti-nociceptive effect consists in the construction of an isobologram that simultaneously evaluates the therapeutic effects of L-arginine and ibuprofen.

In the present invention, we looked for establishing the parameters of assessment and combination of ibuprofen and L-arginine, by developing a pre-clinic study in rats and by constructing isobolograms between the combined therapeutic effects of ibuprofen and L-arginine. In the pre-clinical study, we evaluated also an analgesic composition with (+)S-ibuprofen [(+)S-IBU].

In the pre-clinical study, we evaluated different groups of animals for characterizing the dose-response curves of the two substances. Ibuprofen was administered at doses of 50, 100, 200 and 300 mg/Kg. In the case of L-arginine, its analgesic effect was proved at doses of 5, 50, 100 and 200 mg/Kg. A saline solution was administered as a control for each experimental set. The doses were selected based on the previous pilot experiments, as well as previous literature references with respect to the gastro-protective capacity of L-arginine (Brzozowski and col., 1997).

On the other hand, Tallarida (2000) has demonstrated that for the assessment of the nature of pharmacological interactions, as long as the lineal relation in the log dose-response curve is maintained, it is possible to use any other significant level of the effect. For this reason, we obtained from the dose-response curves, the necessary doses for achieving the 30% ($ED_{30}$) of the maximum possible effect of each drug and of the combination in our inflammatory pain model.

Experimentally, combinations of ibuprofen and L-arginine were administered orally at doses corresponding to different dilutions of the $ED_{30}$ for each drug, and the anti-nociceptive effect of such combinations was evaluated. We used a fixed-ratio scheme.

Figure 1:
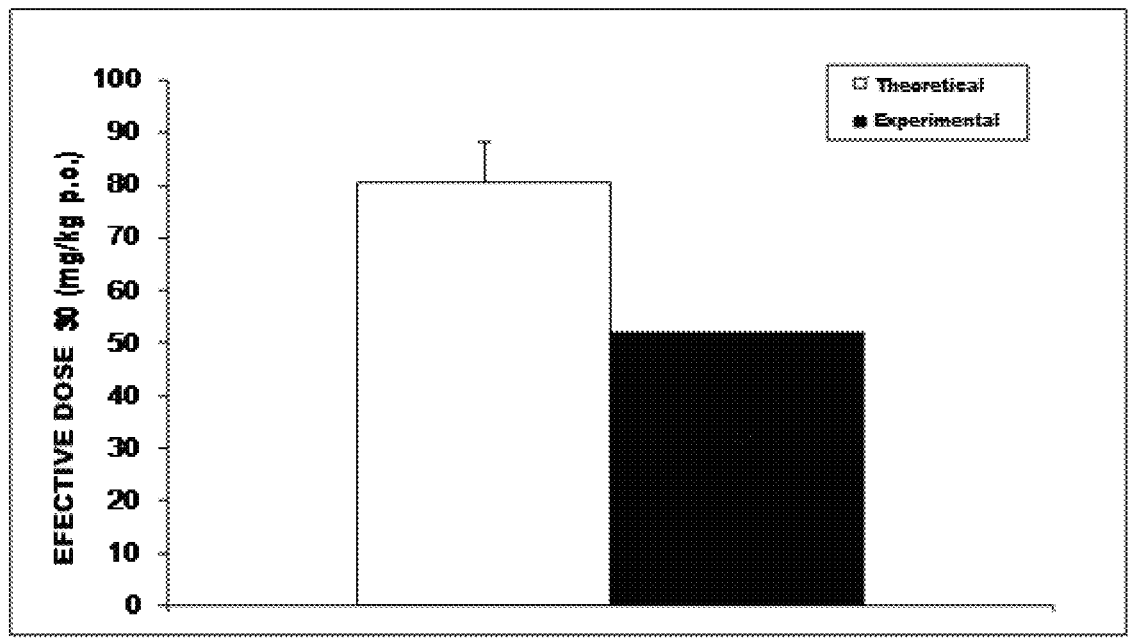

For the assessment of pharmacological interaction it is necessary to consider that when two drugs are administered jointly, there is a need of characterizing the effect of the combination in relation with the effect of each individual drug. A method that allows evaluating the kind of interaction between two drugs is the isobolographic analysis. This method is based on the comparison of the particular doses that are equi-effective. From the dose-effect curves of the individual agents, the respective $ED_{30}$ are obtained. Subsequently, a dose-response curve is obtained after the co-administration of the two drugs in a constant dose ratio, based on the $ED_{30}$ values of the individual agents. From the dose-response curve of the drug combination, the $ED_{30}$ value of the mixture is obtained. Said value is known as the experimental $ED_{30}$. Afterwards, the $ED_{30}$ of the additive theoretical combination is calculated from the sum (weighted) of the individual components. FIG. 1 shows graphically the comparison of the theoretical $ED_{30}$ and the experimental $ED_{30}$. The experimental $ED_{30}$ (52.05±0.07 mg/kg) is considerably lower than the theoretical $ED_{30}$ (80.6±7.6 mg/kg), indicating that the combination of ibuprofen and L-arginine produces synergism in the anti-nociceptive effect in the inflammatory pain model in rats.

Once both the theoretical and experimental $ED_{30}$ values are obtained, a statistical comparison is carried out between the theoretical additive point and the experimental $ED_{30}$ value, by means of the Student's t-test. If the experimental $ED_{30}$ is considerably lower than the theoretical additive $ED_{50}$ (p<0.05), it is considered that the effect of administering the combination results in a synergism in the pharmacological effect. If they are equivalent, it is considered that the effect of the combination is only the sum of the individual effects, but if the experimental $ED_{30}$ is considerably higher than the theoretical $ED_{30}$, an antagonism of a drug over the other would occur.

A visual way of representing the kind of interaction between two drugs, according to the previously described method, is by using isobolograms. The isobolograms were constructed as follows: The values of an effective dose at a significant level, in our case the $ED_{30}$, for each of the individual agents, were plotted in rectangular coordinates (x,y). The line connecting these two points is called isobole or additivity line, and this line contains all the possible combinations of the two drugs, that will produce only an additive or sum effect.

Now, if the experimental point falls above the additivity line, it means that antagonism occurred when co-administrating the two drugs. But if the experimental point falls below this line, it means that the combination of the drugs was translated into the potentiation of the assessed effect.

Finally, for describing the magnitude of the interaction, the interaction index (y) is calculated. This index is a quantitative measure of the interaction between two drugs.

$$\gamma = \frac{\text{Drug 1 Dose in the } EDx \text{ of the combination}}{EDx \text{ of the individual Drug 1}} + \frac{\text{Drug 2 Dose in the } EDx \text{ of the combination}}{EDx \text{ of the individual Drug 2}}$$

Thus, the experimental $ED_{30}$ obtained after administering the combinations was 52.05±0.07 mg/kg, which was considerably lower (p<0.05) than the theoretical additive $ED_{30}$ (the combination dose that only produces an additive effect) of 80.6±7.6 mg/kg. This means that the oral co-administration of (RS)-ibuprofen and L-arginine produces a synergistic interaction, i.e., after an oral co-administration of ibuprofen and L-arginine, the same level of anti-nociceptive effect is achieved (30%) but the doses of both drugs can be reduced in about 1.5 times.

Figure 2:
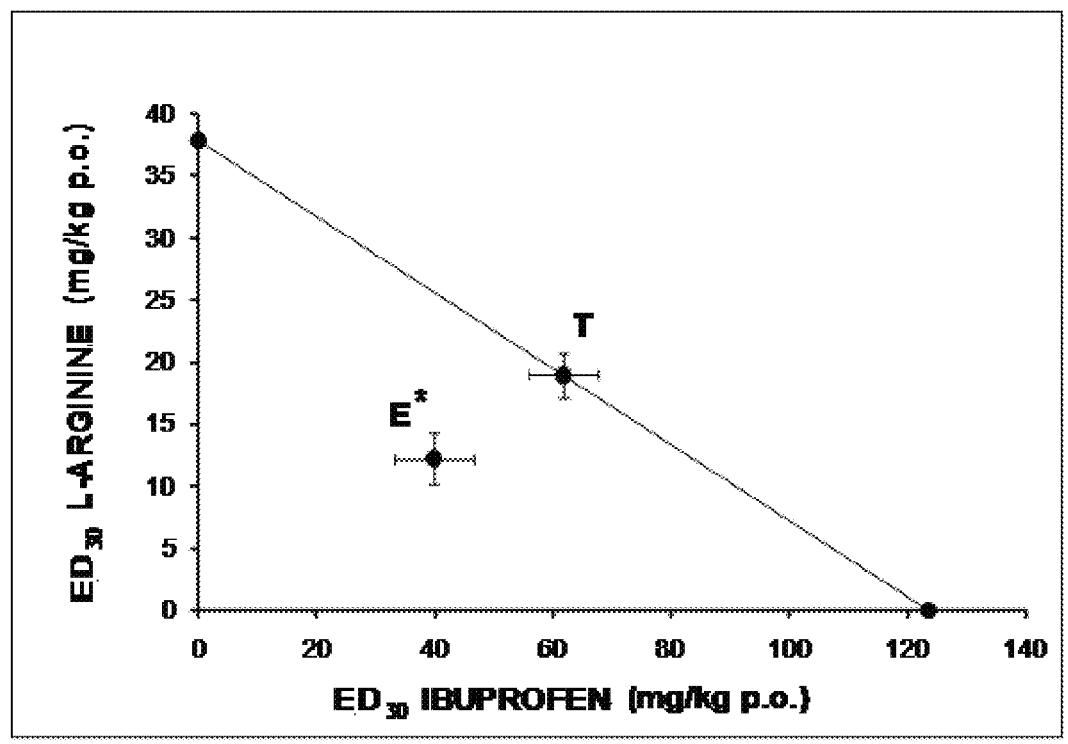

The visual representation of the interaction at a systemic level between the drugs can be clearly observed in the isobologram of FIG. 2, in which the experimental point is very much below the additivity line or isobole, indicating the presence of a synergistic interaction when orally co-administering ibuprofen and L-arginine. In the isobologram of the systemic interaction between ibuprofen and L-arginine, the $ED_{30}$ values for the drugs with their respective standard errors, after the individual administration, are plotted in the x-y axis, respectively. The straight line connecting the $ED_{30}$ of the drugs, contains all the possible combinations between these two agents, that only produce an additive effect (isobole). The "T" point corresponds to the theoretical $ED_{30}$ for this study. The "E" point is the experimental $ED_{30}$ of the combinations, and in this case it is below the isobole, which indicates a synergistic interaction between ibuprofen and L-arginine.

As a result of the assessment of the therapeutic activity of the composition with the enantiomeric form (+)S-Ibuprofen, it exhibited an elevated behavior in its analgesic, anti-inflammatory and antipyretic effect, which is higher than the one shown with the composition of the racemic mixture. For the composition of the present invention, a combination containing (+)S-Ibuprofen and L-arginine with a (+)—IBU/L-ARG ratio between 0.8 and 4.5 can be employed, being the preferred (+)—IBU/L-ARG ratio equal to 2.12.

The combination ibuprofen+L-arginine is administered in different formulations. A preferred one is the oral formulation, due to its convenience when being administered. It can be in the form of a suspension, pill, tablet, granulate, powder or capsule.

A design of the solid composition can be as a pill, tablet, granulate, lozenge, powder or powder for forming reconstituted solution, and in its case, it can contain compressibility vehicle, diluent binder, anti-stacking agent, lubricant, plasticizer and disintegrant in a compartment separated from the outer final coating. An isolating coating or film composed by a coating polymer that confers protection from factors such as humidity, light, among others, is added over the film that contains the active agents.

The combination of the present invention was assessed through pre-clinic studies, where the effectiveness of the association was compared versus associations of ibuprofen and L-arginine in different concentrations, and versus formulations having acetaminophen and diclofenac.

This study demonstrates that the association of ibuprofen and L-arginine in a ratio of IBU/L-ARG=3.26, produces a synergistic effect on the analgesic, anti-inflammatory and anti-pyretic action, with respect to the treatment with the individual drugs or with different proportions of the same active agents.

Assessment of the Anti-Nociceptive Effect.

The study employs a model where pain is induced by means of the sub-cutaneous administration of formalin (1%) in the dorsal zone of the rear right paw of the rat, followed by observation and evaluation of the writhes occurring with the rats used in the study. The behavior of the twitches induced by formalin is biphasic. The acute initial phase (1-10 minutes) is intense and is followed by a relatively short period of inactivity, which is followed by a prolonged response (15-60 minutes).

Figure 3:
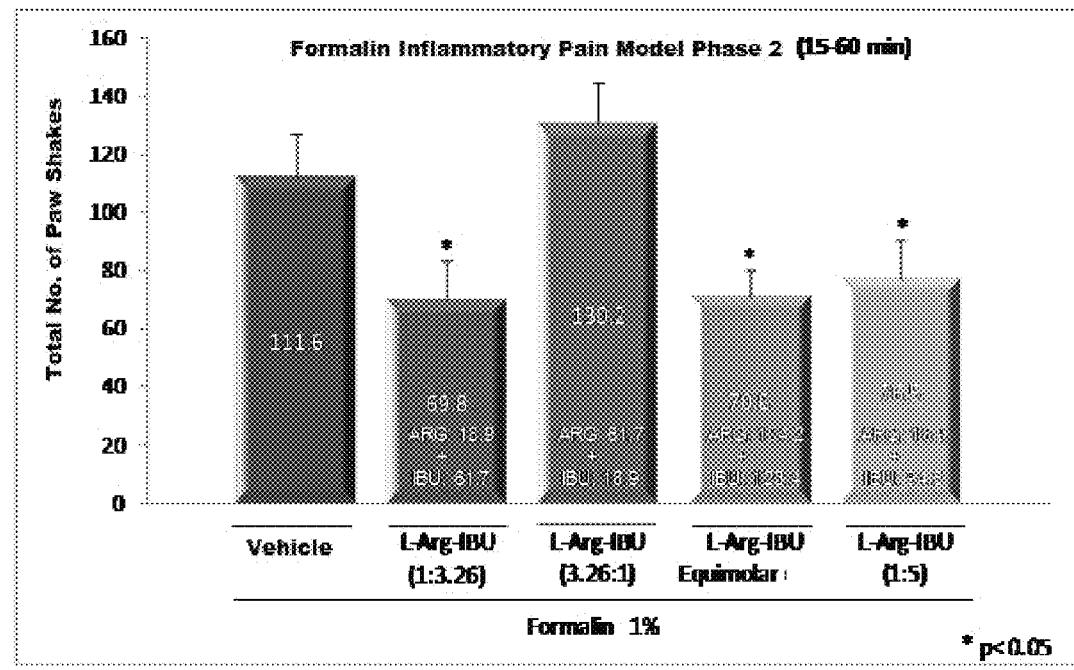

FIG. 3 shows the comparative effect of the combination of L-arginine with ibuprofen in different proportions in the second experimental phase of the inflammatory pain model with formalin. The analgesic effect is expressed as the reduction in the total number of writhes of the rat's paw.

The proposed ratio (IBU/L-ARG=3.26) provoked a better anti-nociceptive response with respect to the inverse ratio (ibuprofen/L-arginine=0.306), or with respect to an equimolar ratio (IBU/L-ARG=1.184), or with respect to a ratio having a higher ibuprofen concentration (IBU/L-ARG=5.0). It is worth mentioning that the combination with the inverse ratio (IBU/L-ARG=0.306) did not reduce the nociceptive behavior, and even is prone to incrementing it.

When evaluating the IBU/L-ARG=5.0 ratio in an attempt of determining if the response would improve in the presence of a higher NSAID concentration, the results suggest that, although a significant analgesia was observed, this response was not different to the one observed with the IBU/L-ARG=3.26 ratio.

Even though most of the commercial forms of ibuprofen consist of the racemic mixture, several studies have demonstrated that the dextrorotatory enantiomer is more efficient. A dose between 50% and 75% of the active enantiomer is considered to be equivalent to 100% of the racemic ibuprofen (Clin Rheumatol. 2001 November; 20 Suppl 1: S22-9 and Eur J Clin Pharmacol (2006) 62:849-854). For this reason, a different interval is claimed in case ibuprofen is present in its dextrorotatory form.

Even though the presented studies were performed with L-arginine, it is assumed that the D enantiomer and the racemic mixture of this amino acid exhibit a similar effect, therefore the present invention is not limited to the use of L-arginine.

Assessment of the Anti-Inflammatory Effect.

Figure 4:
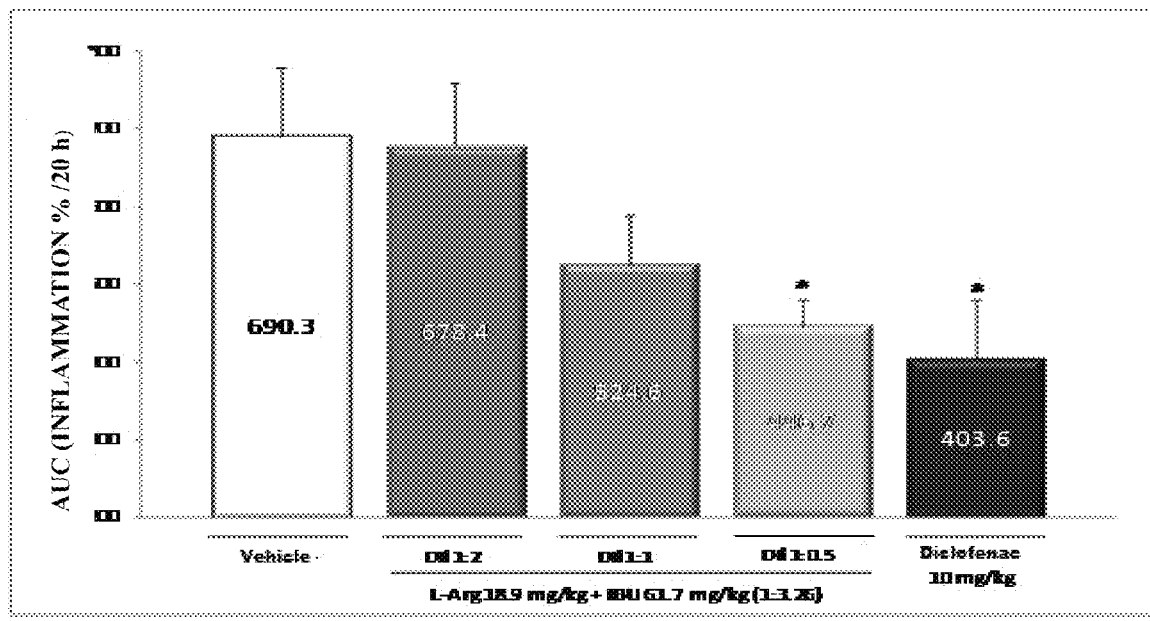
FIG. 4 shows the anti-inflammatory effect measured as a global inhibition of the inflammatory process during the 20-hour observation period. It shows the results obtained with the combination, and the comparison with diclofenac administration.

From the results of the previous study, and following a model where inflammation is induced with carrageenan administration for generating a bruise, we determined the anti-inflammatory effect of the L-ARG-IBU combination, in comparison with the administration of a treatment of known effects (positive control: diclofenac 10 mg/Kg), and of a control group, administered each 8 hours for a period of 48 hours. This model presented a maximum inflammation level of towards 6-8 hours, after which inflammation starts to decrease gradually. FIG. 4 shows the progression of the anti-inflammatory effect measured as a global inhibition of the inflammatory process during the observation period of 20 hours (AUC % inflammation/20 hours) for the combination IBU/L-ARG=3.26 in increasing doses, in comparison with the administration (each 8 hours) of saline solution (control) and in comparison with diclofenac ad ministration (10 mg/kg) in the inflammation model by carrageenan in rats.

None of the treatments modified considerably the inflammatory process before the two hours. However, from the third hour we observed that all of the treatments and mainly the positive control reduced the development of edema.

Once the second dose of the treatments was administered, and thus subsequently during the treatment each eight hours, a discrete anti-inflammatory effect was produced in the case of the low dose of the combination. However, when increasing the dose up to the combination with the dilution IBU/L-ARG=5.0 (IBU:123.4 mg+L-ARG:37.8 mg), an effect similar to the one with diclofenac administration (10 mg/Kg) was achieved.

The results of this part of the study demonstrate that the combination in a ratio of IBU/L-ARG=3.26, repeatedly administered, is able to reduce considerably the inflammatory process induced by carrageenan in rats. The above suggests that the multiple administration of this treatment can be useful in the therapy of processes involving prolonged and/or severe inflammation states, as well as in the treatment of inflammatory pain, independently of the evolution of the inflammatory process per se.

Assessment of the Anti-Pyretic Effect.

Figure 5:
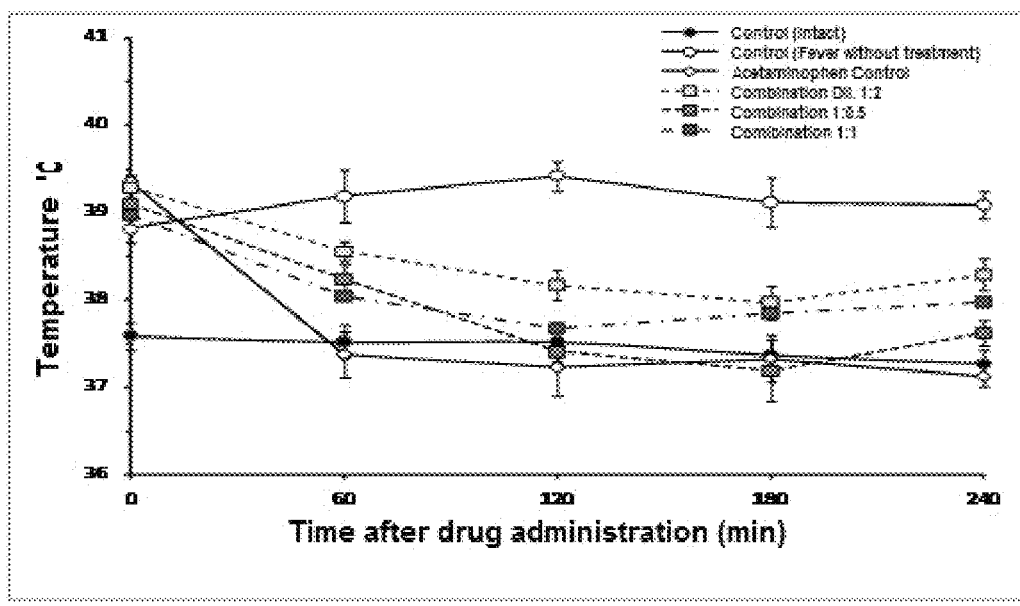
FIG. 5 shows the temporal progression of the anti-pyretic response for the combination IBU/L-ARG=3.26, in increasing doses, in comparison with the administration of saline solution (control) o acetaminophen (15 mg/Kg), in the pyresis model induced by LPS from *E. coli* in rats.

After the assessment of the anti-nociceptive and anti-inflammatory effects, the anti-pyretic effect was assessed for increasing doses of the combination IBU:L-ARG in a ratio IBU/L-ARG=3.26, in comparison with the administration of an agent that is well known as capable of control fever, such as acetaminophen (15 mg/Kg) (see FIG. 5). The results of the study show that in this case, from dilution 1:1 (IBU:61.7 mg/kg+L-ARG:18.9 mg/kg), to dilution 1:0.5 (IBU:123.4 mg/kg+L-ARG:37.8 mg/kg), a reversion on the febrile status from 72% to 90% occurred, i.e., a very important activity takes place, in spite of the relatively low level of the doses of the individual drugs.

FIG. 5 shows that, whereas the non-manipulated group of rats showed an average temperature of 37.45° C., the negative control group (without treatment) exhibited an average temperature of 39.12° C. during the observation period of 4 hours. On the other hand, acetaminophen was employed as a positive control at a dose of 15 mg/Kg, and we observed that with this NSAID dose, the temperature returned to basal levels, and even provoking a mild reduction, from the first 60 minutes following the drug administration.

Figure 6:
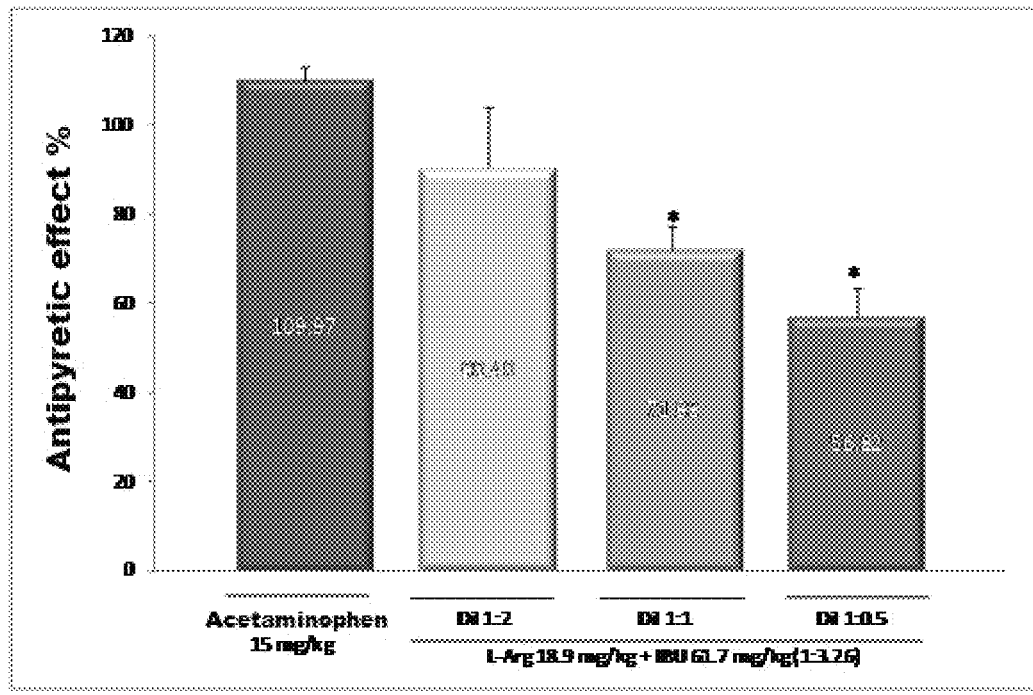
FIG. 6 shows the progression of the average anti-pyretic response in a period of 4 hours, using the pyresis model by sub-cutaneous administration of LPS from *E. coli* in rats. The figure shows a control group, several groups to which the combination ibuprofen+L-arginine (IBU/L-ARG=3.26) was administered in different dilutions, and a group to which acetaminophen was administered (15 mg/Kg).

Regarding the combination of ibuprofen with L-arginine, we observed that, unlike the results in the anti-inflammatory effect, the anti-pyretic effect is important and it achieved statistical significance even from the dilution 1:1 (IBU:61.7 mg/kg+L-ARG:18.9 mg/kg), although the three dose levels produced fever reduction. Thus, considering that acetaminophen generates a total fever reversion, we could estimate that the combination in its dilutions 1:0.5, 1:1 and 1:2 produces a dose-dependent anti-pyretic effect of 56.8, 71.9 and 90.4%, respectively, as shown in FIG. 6.

FIG. 7 is a graph showing the interaction index for the anti-nociceptive effect resulting from the administration of the combination of ibuprofen and L-arginine in different proportions. The dots represent the sets of experimental data, whereas the line represents an interpolation as will be described hereinbelow.

When assessing the effectiveness of different doses of mixtures with the aforementioned proportions, we observe that the interaction index is lower than one for the proportions IBU/L-ARG=5.0 and 3.26, whereas for the equimolar ratio (IBU/L-ARG=1.18), the interaction index is 1.94. Assuming a parabolic behavior in this parameter, an extrapolation of the experimental data allows inferring a synergistic effect in the interval between 1.6 and 5.6 of IBU/L-ARG.

The shaded zone in FIG. 7 shows the composition interval that is expected to have a synergistic behavior.

Finally, the safety aspect of a medicament must also be considered. In this sense, none of the combinations or compounds employed in the experimental series of the present study conducted to motion, autonomous or central response disturbances, that could be appreciated by direct observation.

From all the aforementioned, it is concluded that the combination of ibuprofen with L-arginine presents synergism in the anti-nociceptive effect, whose magnitude depends on the employed ratio, being such ratio IBU/L-ARG equivalent to 3.26 in the instant application. On the other hand, there is evidence that the presence of L-arginine increases the antipyretic effect of ibuprofen, i.e., the combination presents a higher potential as antipyretic agent than as anti-inflammatory agent, aside from showing a favorable anti-nociceptive profile that places it as a promising tool for pain and fever therapeutics.

Based on this pre-clinical study, we can conclude that the combination of ibuprofen with L-arginine is a good alternative for the treatment of pain and it is fully justified.

Based on the above description, the present invention presents a combination indicated in the prevention and treatment of pain from moderate to severe, whose presentation can be made with different proportions of ibuprofen and L-arginine.

The obtained formulations do not limit the content of the active agents to the formulations presented as examples, since the same can be presented with variants of ibuprofen and L-arginine.

A preferred combination without limiting the scope of the present invention is the one that contains 3.26 parts of ibuprofen per one part of L-arginine.

The present invention, compared to the existing products having NSAIDs alone, is expected to have minor adverse effects, due to the low dose of the employed ibuprofen, without jeopardizing the therapeutic effect, since ibuprofen acts synergistically with L-arginine in the treatment of pain.

The present invention is a combination that can be presented in a variant of solid administration, for example, a tablet, oral solution or suspension are not limitative of its presentation and can be applied to other pharmaceutical forms, such as capsules with microspheres, microcapsules or other spherical or non-spherical particulate systems and some other solid pharmaceutical forms in tablets.

By virtue of the above, the present invention renders oral pharmaceutical compositions comprising ibuprofen and L-arginine in the same dose unit, without jeopardizing their release, which are useful in the treatment of pain from moderate to severe, with the reduction of the incidence and severity of adverse effects.

The invention has been sufficiently described so that a person with ordinary knowledge in the matter may reproduce and obtain the results mentioned in this document. However, any person skilled in the technical field related to the present invention can be able to carry out modifications that have not been described in the present application. Therefore, if for the application of these modifications in a particular composition the matter claimed in the following clauses is required, said compositions must be comprised within the scope of the present invention.

The invention claimed is:

1. A synergistic pharmaceutical combination for treating pain, comprising ibuprofen and L-arginine, wherein the ibuprofen/L-arginine weight ratio is between 3.26 and 5.0.

2. A synergistic pharmaceutical combination for treating pain, comprising ibuprofen and L-arginine, wherein the ibuprofen/L-arginine weight ratio is approximately equal to 3.26.

3. A solid pharmaceutical composition comprising the combination according to claim 1, and pharmaceutically acceptable excipients.

4. The pharmaceutical composition of claim 3, wherein the composition is adapted for oral administration.

5. The pharmaceutical composition of claim 3, wherein the composition is in the form of a suspension, pill, tablet, granulate, powder or capsule.

6. The combination according to claim 1, wherein ibuprofen is the enantiomer (+)S-ibuprofen.

7. A solid pharmaceutical composition comprising the combination according to claim 2, and pharmaceutically acceptable excipients.

8. The pharmaceutical composition of claim 7, wherein the composition is adapted for oral administration.

9. The pharmaceutical composition of claim 7, wherein the composition is in the form of a suspension, pill, tablet, granulate, powder or capsule.

10. The combination according to claim 2, wherein ibuprofen is the enantiomer (+)S-ibuprofen.

* * * * *